United States Patent [19]

Müller et al.

[11] 4,158,670
[45] Jun. 19, 1979

[54] PROCESS FOR THE MANUFACTURE OF AROMATIC SULPHONIC ACID ESTERS OF AROMATIC AMINO-HYDROXY COMPOUNDS

[75] Inventors: Rolf Müller, Karben; Joachim Ribka, Offenbach am Main; Horst Tappe, Dietzenbach, all of Fed. Rep. of Germany

[73] Assignee: Cassella Aktiengesellschaft, Frankfurt, Fed. Rep. of Germany

[21] Appl. No.: 879,852

[22] Filed: Feb. 22, 1978

[30] Foreign Application Priority Data

Apr. 21, 1977 [DE] Fed. Rep. of Germany ....... 2717708

[51] Int. Cl.$^2$ ............................................. C07C 143/68
[52] U.S. Cl. ................................................... 260/456 A
[58] Field of Search ..................................... 260/456 A

[56] References Cited

U.S. PATENT DOCUMENTS

| | | | |
|---|---|---|---|
| 1,850,526 | 3/1932 | Zitscher et al. | 260/456 A |
| 3,847,983 | 11/1974 | Kobayashi et al. | 260/456 A |

OTHER PUBLICATIONS

Dehmlow, Chemtech, pp. 210–218 (1975).

Primary Examiner—Nicky Chan
Attorney, Agent, or Firm—Connolly and Hutz

[57] ABSTRACT

A process for the manufacture of esters of aromatic sulphonic acids and aromatic aminohydroxy compounds, of the formula I $$H_2N\text{—}A\text{—}O\text{—}SO_2\text{—}B \qquad (I)$$

comprising reacting an aromatic aminohydroxy compound of the formula II $$H_2N\text{—}A\text{—}OH \qquad (II)$$

having a $pK_a$ value of from 8.5 to 10.1, with a sulphochloride of the formula III $$Cl\text{—}SO_2\text{—}B \qquad (III)$$

wherein
A is phenylene, substituted phenylene, naphthylene or substituted naphthylene,
B is phenyl, substituted phenyl, naphthyl or substituted naphthyl, and both A and B are free from —COOH and —SO$_3$H substituents;
the reaction taking place in a reaction medium consisting essentially of water and a water-immiscible organic solvent for the sulphochloride,
at a temperature of from 0° to 95° C., at a pH which is determined from and associated with the $pK_a$ value of said aromatic aminohydroxy compound of formula II by the equation $$pK_a - pH = 0.5 \text{ to } -1.5,$$

and in the presence of a phase transfer catalyst.

14 Claims, No Drawings

PROCESS FOR THE MANUFACTURE OF AROMATIC SULPHONIC ACID ESTERS OF AROMATIC AMINO-HYDROXY COMPOUNDS

The present invention relates to a process for the manufacture of esters of aromatic sulphonic acids with aromatic aminohydroxy compounds, of the general formula I

wherein A and B are aromatic nuclei which can optionally carry further substituents but which are free from COOH groups and SO₃H groups, in which an aromatic aminohydroxy conpound of the formula II

wherein A is an aromatic nucleus which can be substituted as indicated above, the $pK_a$ value of which is between 8.5 and 10.1, is reacted with a sulphochloride of the formula III

wherein B is also an aromatic nucleus which can be substituted as indicated above, in a system consisting of water and an organic solvent which is not water-miscible, at a particular pH value, which depends on the $pK_a$ value of the aromatic aminohydroxy compound employed, in the presence of a phase transfer catalyst.

Compounds of the general formula I are valuable intermediate products for organic syntheses; they are outstandingly suitable, for example, as diazo components for the manufacture of disperse azo dyestuffs (compare German Offenlegungsschrift No. 1,817,977).

In general, these valuable compounds of the formula I have hitherto been manufactured by multi-stage processes. Thus, for example, aromatic nitrohydroxy compound were reacted with aromatic sulphochlorides to give the corresponding nitrosulphonic acid esters, the nitro group of which was then reduced to the amino group in a second process stage.

(L. C. Raiford and J. R. Shelton, J. Amer. Chem. Soc. volume 65, page 2,048 (1943); and J. V. Aleksandrow and Yu. S. Abradushkin, Zh. Obshch. Khim. volume 31, page 3,610 (1961), CA 57, page 9,719 (1961)).

In another process, which uses aromatic aminohydroxy compounds as the starting material, the amino group is first protected, for example by acylation, the hydroxy group is then reacted with the sulphochloride to give the sulphonic acid ester in a second process stage and finally the protective group is split off again from the amino group in a third process stage.

It is possible to manufacture sulphonic acid esters of phenols which are free from amino groups by direct reaction with sulphochlorides (M. Georgescu, Berichte der Deutschen Chemischen Gesellschaft 24, 414 (1891)). However, this simple process cannot be applied to aminophenols since the amino group itself is capable of reacting with sulphochlorides and therefore considerably interferes with the desired course of the reaction.

Thus it is indeed known that, for example, nitroaminophenols, the nitro group of which is in the ortho-position or para-position relative to the OH group, can be directly reacted with aromatic sulphonic acid chlorides in the region of about pH 7 to give sulphonic acid esters. However, this process fails in cases in which the aminophenol to be esterified is free from o-nitro groups or p-nitro groups or other second order substituents having an analogous action. By this process, aminophenols without second order substituents in the nucleus give only unsatisfactory yields and highly impure end products which cannot be used for further syntheses or can be used for further syntheses only after troublesome purification operations. In the case of m-aminophenol, in particular, it is known (F. Reverdin and A. de Luc, Berichte der Deutschen Chemischen Gesellschaft 47, 1,538 (1914) that in an acetate-buffered aqueous-alcoholic medium it is N-acylated by sulphochlorides, that is to say forms the sulphamide as virtually the sole product.

There was therefore an urgent need for a simple process for the manufacture of aromatic sulphonic acid esters of aromatic aminohydroxy compounds which are free from second order substituents having a powerful negative influence.

It has now been found, surprisingly, that esters of aromatic aminohydroxy compounds with aromatic sulphonic acids, of the general formula I

wherein A is phenylene or naphthylene and B is phenyl or naphthyl, and A and B can carry further substituents but are free from —COOH groups and —SO₃H groups, (if —COOH or SO₃H groups are present the reaction is not feasible), can be obtained with excellent yields and in very high purity when an aromatic aminohydroxy compound of the formula II

wherein A is phenylene or naphthylene which can be substituted as indicated above, the $pK_a$ value of which is between 8.5 and 10.1, is reacted with a sulphochloride of the formula III

wherein B is phenyl or naphthyl which can be substituted as indicated above, in a system consisting of water and an organic solvent which is not water-miscible, at temperatures from 0° to 95° C. and a pH value which is linked with the $pK_a$ value of the aromatic aminohydroxy compound employed by the equation $$pK_a - pH = +0.5 \text{ to } -1.5,$$

in the presence of a phase transfer catalyst.

The process according to the invention can be advantageously employed both for the manufacture of compounds of the formula I which are unsubstituted in the nuclei A and B and for the manufacture of those which are substituted in the nuclei A and B.

Thus phenylene or naphthylene represented by A can carry one to 3 identical or different substituents from the following group: halogen, alkyl with 1 to 6 C atoms, cycloalkyl with 3-6 C atoms, alkenyl with 2 to 6 C atoms, phenyl, alkoxy with 1 to 6 C atoms and alkanoyl with a total of 1 to 7 C atoms.

Typical examples for A are:

phenylene, naphthylene, chloro phenylene, fluoro phenylene, bromo phenylene, dichloro phenylene, dibromo phenylene, chlorobromo phenylene, methyl phenylene, ethyl phenylene, hexylphenylene, cyclohexyl phenylene, vinyl phenylene, allyl phenylene, dimethyl phenylene, methyl-butyl phenylene, methylhexyl phenylene, ethyl-propyl phenylene, methyl-vinyl phenylene, methyl-allyl phenylene, ethyl-chloro phenylene, propylchloro phenylene, methyl-fluoro phenylene, methyl-chlorovinyl phenylene, methyl-bromo phenylene, cyclohexyl-fluoro phenylene, phenyl phenylene, methoxy phenylene, ethoxy phenylene, acetyl phenylene, butyryl phenylene, benzoyl phenylene, valeryl phenylene.

The process of the present invention is particularly suitable for the manufacture of compounds of the formula I in which a phenylene or naphthylene represented by A is either unsubstituted or carries one substituent from the following group: alkyl with 1 to 3 C atoms, fluorine, chlorine and bromine, in particular chlorine.

If B in the formula I represents phenyl, it can be substituted by one to 2 identical or different substituents of the following group: halogen, nitro, cyano, alkyl with 1 to 6 C atoms and alkanoyl with a total of 1 to 6 C atoms.

If B in the formula I represents naphthyl, this can contain one substituent from the following group: halogen, in particular fluorine, chlorine and bromine, preferably chlorine, nitro, cyano and alkyl with 1 to 6 C atoms.

Typical examples for B are: phenyl, naphthyl, chloro phenyl, fluoro phenyl, bromo phenyl, dichloro phenyl, nitro phenyl, cyano phenyl, methyl phenyl, ethyl phenyl, hexyl phenyl, acetyl phenyl.

B preferably denotes phenyl which optionally carries one substituent from the group fluorine, chlorine, bromine or alkyl with 1 to 6 C atoms.

The substituents of A and B can in turn carry further substituents.

Alkyl groups and alkoxy groups which are substituents of A or B can contain the following substituents: halogen, in particular fluorine, chlorine or bromine, cyano, alkoxy with 1 to 2 C atoms, alkylmercapto with 1 to 6 C atoms, alkylsulphonyl with 1 to 6 C atoms, halogenoalkylsulphonyl, in particular with 2 to 6 C atoms, in particular chloroalkylsulphonyl, and alkenylsulphonyl with 2 to 6 C atoms.

Alkanoyl groups which are substituents of A or B can in turn contain the following substituents: halogen, in particular fluorine, chlorine or bromine, and alkoxy with 1 to 6 C atoms.

If they are present at all, the substituents mentioned for substituents of the nuclei A and B are as a rule present as a single substituent. The simple substituents chlorine or lower alkoxy, two of which, identical or different, can also be contained in the substituents of A or B. Examples of this type of polysubstituted substituents of A and B are:

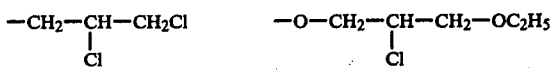

The substituents of A and B can be polysubstituted by the substituent fluorine. The trifluoromethyl group is an example of a substituent of A and B polysubstituted by fluorine.

Compounds of the formula I which contain particular substituents in A and B are manufactured by choosing the starting materials of the formula II and III so that these already contain the desired substituents in the nuclei A and B.

Examples of aromatic aminohydroxy compounds of the formula II which can be esterified by the process according to the invention are:

(a) Compounds of the formula

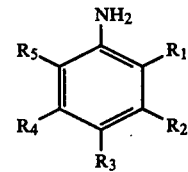

wherein $R_1$–$R_5$ have the following meaning

| $R_1$ | $R_2$ | $R_3$ | $R_4$ | $R_5$ |
|---|---|---|---|---|
| OH | H | H | H | H |
| OH | Cl | H | H | H |
| OH | H | Cl | H | H |
| OH | H | H | Cl | H |
| OH | H | H | H | Cl |
| OH | F | H | H | H |
| OH | H | F | H | H |
| OH | H | H | F | H |
| OH | H | H | H | F |
| OH | Br | H | H | H |
| OH | H | Br | H | H |
| OH | H | H | Br | H |
| OH | H | H | H | Br |
| OH | Cl | Cl | H | H |
| OH | H | Cl | Cl | H |
| OH | H | H | Cl | Cl |
| OH | Cl | H | Cl | H |
| OH | Cl | H | H | Cl |
| OH | H | Cl | H | Cl |
| OH | Br | Br | H | H |
| OH | H | Br | Br | H |
| OH | H | H | Br | Br |
| OH | Br | H | Br | H |
| OH | Br | H | H | Br |
| OH | H | Br | H | Br |
| OH | Cl | Br | H | H |
| OH | Cl | H | Br | H |
| OH | Cl | H | H | Br |

-continued

| R₁ | R₂ | R₃ | R₄ | R₅ |
|----|----|----|----|----|
| OH | H | Cl | H | Br |
| OH | H | H | Cl | Br |
| OH | Br | Cl | H | H |
| OH | Br | H | Cl | H |
| OH | Br | H | H | Cl |
| OH | H | Br | Cl | H |
| OH | H | Br | H | Cl |
| OH | CH₃ | H | H | H |
| OH | H | CH₃ | H | H |
| OH | H | H | CH₃ | H |
| OH | H | H | H | CH₃ |
| OH | C₂H₅ | H | H | H |
| OH | H | C₂H₅ | H | H |
| OH | H | H | C₂H₅ | H |
| OH | H | H | H | C₂H₅ |
| OH | C₆H₁₃ | H | H | H |
| OH | H | C₆H₁₃ | H | H |
| OH | H | H | C₆H₁₃ | H |
| OH | H | H | H | C₆H₁₃ |
| OH | C₆H₅ | H | H | H |
| OH | H | C₆H₅ | H | H |
| OH | H | H | C₆H₅ | H |
| OH | H | H | H | C₆H₅ |
| OH | CH=CH₂ | H | H | H |
| OH | H | CH=CH₂ | H | H |
| OH | H | H | CH=CH₂ | H |
| OH | H | H | H | CH=CH₂ |
| OH | CH₂—CH=CH₂ | H | H | H |
| OH | H | CH₂—CH=CH₂ | H | H |
| OH | H | H | CH₂—CH=CH₂ | H |
| OH | H | H | H | CH₂—CH=CH₂ |
| OH | CH₃ | CH₃ | H | H |
| OH | CH₃ | H | CH₃ | H |
| OH | CH₃ | H | H | CH₃ |
| OH | H | CH₃ | CH₃ | H |
| OH | H | CH₃ | H | CH₃ |
| OH | H | H | CH₃ | CH₃ |
| OH | H | CH₃ | C₄H₉ | H |
| OH | CH₃ | C₆H₁₃ | H | H |
| OH | C₂H₅ | C₃H₇ | H | H |
| OH | CH₃ | CH=CH₂ | H | H |
| OH | H | CH₃ | CH₂—CH=CH₂ | H |
| OH | Cl | C₂H₅ | H | H |
| OH | C₃H₇ | Cl | H | H |
| OH | H | F | CH₃ | H |
| OH | Cl | CH=CH₂ | CH₃ | H |
| OH | H | CH₃ | Br | H |
| OH | H | F | H | H |
| OH | C₆H₅ | H | H | H |
| OH | OCH₃ | H | H | H |
| OH | H | OCH₃ | H | H |
| OH | H | H | OCH₃ | H |
| OH | H | H | H | OCH₃ |
| OH | OC₂H₅ | H | H | H |
| OH | H | OC₂H₅ | H | H |

-continued

| $R_1$ | $R_2$ | $R_3$ | $R_4$ | $R_5$ |
|---|---|---|---|---|
| OH | H | H | $OC_2H_5$ | H |
| OH | H | H | H | $OC_2H_5$ |
| OH | $-CO-CH_3$ | H | H | H |
| OH | H | $CO-CH_3$ | H | H |
| OH | H | H | $CO-CH_3$ | H |
| OH | $CO-C_3H_7$ | H | H | H |
| OH | H | $CO-C_3H_7$ | H | H |
| OH | H | H | H | $CO-C_3H_7$ |
| OH | $CO-C_6H_5$ | H | H | H |
| OH | H | $CO-C_6H_5$ | H | H |
| OH | H | H | $CO-C_6H_5$ | H |
| OH | H | H | H | $CO-C_6H_5$ |
| OH | $CO-C_4H_9$ | H | H | H |
| OH | H | $CO-C_4H_9$ | H | H |
| OH | H | H | $CO-C_4H_9$ | H |
| OH | H | H | H | $CO-C_4H_9$ |
| H | OH | H | H | H |
| Cl | OH | H | H | H |
| H | OH | Cl | H | H |
| H | OH | H | Cl | H |
| H | OH | H | H | Cl |
| F | OH | H | H | H |
| H | OH | F | H | H |
| H | OH | H | F | H |
| H | OH | H | H | F |
| Br | OH | H | H | H |
| H | OH | Br | H | H |
| H | OH | H | Br | H |
| H | OH | H | H | Br |
| Cl | OH | Cl | H | H |
| Cl | OH | H | Cl | H |
| Cl | OH | H | H | Cl |
| H | OH | Cl | Cl | H |
| H | OH | Cl | H | Cl |
| H | OH | H | Cl | Cl |
| $CH_3$ | OH | H | H | H |
| H | OH | $CH_3$ | H | H |
| H | OH | H | $CH_3$ | H |
| H | OH | H | H | $CH_3$ |
| $C_6H_{13}$ | OH | H | H | H |
| H | OH | $C_6H_{13}$ | H | H |
| H | OH | H | $C_6H_{13}$ | H |
| H | OH | H | H | $C_6H_{13}$ |
| H | OH | ⬡H | H | H |
| H | OH | H | ⬡H | H |
| H | OH | H | H | ⬡H |
| H | OH | $CH=CH_2$ | H | H |
| H | OH | H | $CH=CH_2$ | H |
| H | OH | H | H | $CH=CH_2$ |
| $OCH_3$ | OH | H | H | H |
| H | OH | $OCH_3$ | H | H |
| H | OH | H | $OCH_3$ | H |
| H | OH | H | H | $OCH_3$ |
| $OC_2H_5$ | OH | H | H | H |
| H | OH | $OC_2H_5$ | H | H |
| H | OH | H | $OC_2H_5$ | H |
| H | OH | H | H | $OC_2H_5$ |
| H | OH | $CO-CH_3$ | H | H |
| H | OH | H | $CO-CH_3$ | H |
| H | OH | H | H | $CO-CH_3$ |
| H | OH | H | $CO-C_3H_7$ | H |
| H | OH | H | $CO-C_6H_5$ | H |

(b) Starting materials II of the napthalene series are, for example:

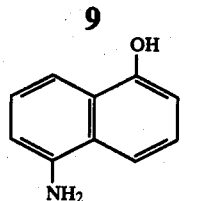

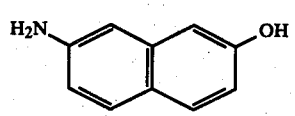

The process according to the invention is particularly suitable for the esterification of aminophenols with only one substituent from the group methyl, ethyl, methoxy, ethoxy and chlorine. m-Aminophenol is a particularly preferred starting material for the process according to the invention.

Examples of aromatic sulphonic acid chlorides which can advantageously be reacted with the aminohydroxy compounds by the process according to the invention are:

(a) Compounds of the formula

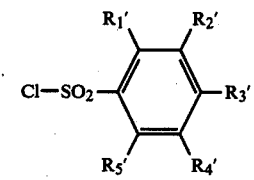

wherein $R_1'$–$R_5'$ have the following meaning:

| $R_1'$ | $R_2'$ | $R_3'$ | $R_4'$ | $R_5'$ |
|---|---|---|---|---|
| Cl | H | H | H | H |
| H | Cl | H | H | H |
| H | H | Cl | H | H |
| H | H | H | F | H |
| H | H | F | H | H |
| F | H | H | H | H |
| Br | H | H | H | H |
| H | Br | H | H | H |
| H | H | Br | H | H |
| Cl | H | Cl | H | H |
| Cl | H | H | Cl | H |
| H | NO$_2$ | H | H | H |
| H | H | NO$_2$ | H | H |
| CN | H | H | H | H |
| H | CN | H | H | H |
| H | H | CN | H | H |
| H | CH$_3$ | H | H | H |
| H | H | CH$_3$ | H | H |
| H | C$_2$H$_5$ | H | H | H |
| H | H | C$_2$H$_5$ | H | H |
| H | C$_6$H$_{13}$ | H | H | H |
| H | H | C$_6$H$_{13}$ | H | H |
| H | CO—CH$_3$ | H | H | H |
| H | H | CO—CH$_3$ | H | H |

An example of a sulphonic acid chloride of the naphthalene series is naphthalene-2-sulphonic acid chloride of the formula

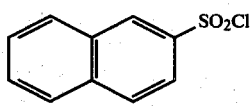

Benzenesulphonyl chlorides which contain only halogen atoms or alkyl groups as substituents are particularly suitably for reaction by the process according to the invention. In addition to benzenesulphonyl chloride itself, those derivatives which contain only one lower alkyl radical or 1 chlorine atom as substituents of the nucleus B, in particular para-toluenesulphonyl chloride and para-chlorobenzenesulphonyl chloride, are particularly preferred.

The process according to the invention is carried out by bringing the reactants together under the abovementioned reaction conditions according to the invention in the 2-phase system consisting of water and an organic solvent which is not water-miscible. Thus, in principle, it is possible, for example, to mix all the required components of the reaction mixture in the required proportions from the beginning if a trouble-free course of the reaction is ensured by means of suitable measures, that is to say that in this case it must be ensured that the removal of heat is sufficient and frothing over is prevented.

In order to avoid, from the beginning, difficulties in carrying out the reaction, an embodiment of the process according to the invention can be chosen in which one of the starting products is initially introduced into the solvent system and the second is metered in over an appropriate period.

The process according to the invention is therefore as a rule carried out by initially introducing the aromatic aminohydroxy compound to be esterified, in an aqueous alkaline solution or suspension which is adjusted to the desired pH value, into a suitable reaction vessel together with the organic solvent which is not water-miscible and the phase transfer catalyst, and then gradually adding the aromatic sulphochloride at the desired reaction temperature, it being ensured that the reaction mixture is mixed thoroughly and vigorously, for example by rapid stirring. The sulphochlorides employed in carrying out the process according to the invention can be used either in the pure form or dissolved in an organic solvent. It is particularly advantageous to use a solution if sulphochlorides which are solid at room temperature are to be employed, since they can be metered into the reaction mixture more uniformly in the form of a solution. The solvent used for the sulphochlorides to be employed is appropriately the same as that which forms the organic phase of the 2-phase system to be employed according to the invention.

The aromatic aminohydroxy compounds of the general formula II are reacted with the aromatic sulphochlorides of the general formula III in a two-phase system consisting of water and an organic solvent which is not water-miscible, by the process according to the invention. Possible organic solvents which are not water-miscible are aliphatic hydrocarbons with up to 10, preferably 7, carbon atoms, in particular the representatives of this series which are liquid at room temperature and mixtures of these hydrocarbons which are liquid at room temperature, appropriately those with boiling points between 50° and 180° C., preferably between 50° and 100° C., liquid halogenohydrocarbons with up to 6 carbon atoms and up to 4 chlorine atoms, benzene, alkylbenzenes with 1 to 3 alkyl radicals each with 1 to 3 carbon atoms and halogenobenzenes, in particular chlorobenzenes with 1 to 3 halogen atoms, in particular chlorine atoms.

Examples of solvents which can be employed for the process according to the invention are pentane, hexane, heptane, octane, nonane, decane, petroleum ether, light petrol and heavy petrol, ethylene chloride, chloroform, dichloroethane, trichloroethylene, perchloroethylene, benzene, toluene, ortho-, meta- and para-xylene, ethylbenzene, diethylbenzene, isopropyl-benzene, monochlorobenzene, monobromobenzene, ortho-dichlorobenzene, meta-dichlorobenzene and ortho-, meta- or para-chlorotoluene.

Particularly suitable water-immiscible organic solvents for carrying out the process according to the invention are the aliphatic chlorohydrocarbons, in particular dichloroethane, trichloroethylene and perchloroethylene, and the aromatic hydrocarbons, in particular benzene, toluene and o-, m- and p-xylene (also in the form of their industrial mixtures), monochlorobenzene and o-dichlorobenzene. Monochlorobenzene is particularly preferred.

The process according to the invention is carried out in a quite specific pH range which depends on the $pK_a$ value of the aromatic aminohydroxy compound employed as the starting material. There is the following connection between this $pK_a$ value and the pH value at which the process according to the invention is carried out:

$$pK_a - pH = +0.5 \text{ to } -1.5$$

Solving this equation for the pH value gives the formula $$pH = pK_a - 0.5 \text{ to } pK_a + 1.5$$

from which it can be seen that the pH range within which the process according to the invention is carried out for a specific starting substance with a given $pK_a$ value is 0.5 units below to 1.5 units above the numerical value of this particular $pK_a$ value relevant for the starting material. For example, if a starting material with a $pK_a$ value of 9 is employed, the esterification by the process according to the invention can be carried out in the range from pH 8.5 to pH 10.5.

The esterification is preferably carried out at a pH value of $$pH = pK_a \pm 0 \text{ to } pK_a + 1.2,$$

and in particular at $$pH = pK_a + 0.7 \text{ to } pK_a + 1.0.$$

The required pH value is achieved by adding bases to the reaction medium. Suitable bases are compounds which have a pH value greater than 11 in an aqueous molar solution. It is particularly appropriate to employ alkali metal hydroxides and alkaline earth metal hydroxides, in particular sodium hydroxide or potassium hydroxide.

According to the equation

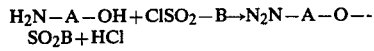

hydrochloric acid is liberated when carrying out the process according to the invention and this would rapidly shift the pH value initially set up out of the range to be maintained according to the invention. It is therefore necessary to trap the hydrochloric acid formed by means of buffer substances. Compound which buffer in the pH range from 10 to 11 are used as buffers. Alkaline earth metal carbonates and alkali metal carbonates, in particular sodium carbonate or potassium carbonate, preferably sodium carbonate, are particularly suitable.

In principle, the addition of these buffer substances can be omitted if the hydrochloric acid formed during the reaction is trapped during the reaction by the successive addition of alkali. The rate of the alkali addition is regulated here so that the desired pH value initially set up in the mixture remains constant. However, it is very advantageous to carry out the reaction in the presence of a buffer substance, even when alkali is successively added, since it prevents large local variations, and large variations with time, in the pH value caused by unavoidable irregularities in the alkali addition.

A further characteristic of the present process which is essential to the invention is the use of phase transfer catalysts. Phase transfer catalysts have hitherto preferably been employed to facilitate alkylation reactions. The article by E. V. Dehmlow in "Angewandte Chemie" International Edition, English volume 13, page 170, 1974, for example, contains a summarising survey of phase transfer catalysis and phase transfer catalysts. Phase transfer catalysts which can be used for carrying out the process according to the invention are, in particular, quaternary ammonium salts or phosphonium salts of the formula IV and V

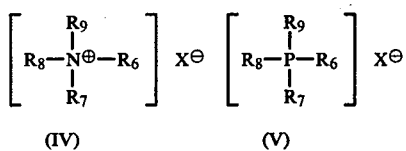

In these formulae, $R_6$ to $R_9$ denote alkyl with 1 to 16 C atoms, hydroxyalkyl with 2 to 16 C atoms, preferably 2 to 4 C atoms, or alkoxyalkyl with 1 to 16 C atoms, preferably 2 to 6 C atoms, phenyl, alkylphenyl with 1 to 10 C atoms in the alkyl radical, benzyl or phenethyl and $X^\ominus$ denotes the ions $F^\ominus$, $Cl^\ominus$, $Br^\ominus$, $SO_4^{\ominus\ominus}$, $HSO_4^\ominus$, $SO_3^{\ominus\ominus}$ and $HSO_3^\ominus$.

Particularly suitable phase transfer catalysts for the intended use according to the invention are, for example, di-(dodecyl)-dimethylammonium chloride, hexadecyltrimethylammonium chloride, tetrabutylammonium chloride, trioctylmethylammonium chloride, tris-decylmethylammonium chloride and trialkyl-($C_8$-$C_{10}$ mixture)-methylammonium chloride. Trialkyl-($C_8$-$C_{10}$ mixture)-methylammonium chloride and tetrabutylammonium chloride are particularly preferably employed according to the invention.

The amount of phase transfer catalyst to be employed is appropriately 0.2 to 2.5 mol%, relative to the amount of aromatic aminohydroxy compound employed. 0.5 to 2 mol%, in particular 1 mol%, of the phase transfer catalyst are preferably employed.

The process according to the invention is carried out at temperatures between 0° and 95° C. The temperature range from 20° to 50° C., preferably that from 35° to 40° C., is particularly favourable.

The reaction temperature is appropriately chosen below the boiling point of the organic solvent which is not water-miscible. However, it is also possible to carry out the reaction at the boiling point of the azeotrope of the organic solvent and water. It is less appropriate to carry out the process according to the invention at temperatures above the boiling point of the organic solvent, since in this case the reaction must be carried out under excess pressure in a reaction vessel which is sealed pressure-tight.

After the reaction has ended, the reaction mixtures are worked up in a manner which is in itself known. The reaction product is appropriately transferred to the aqueous phase of the two-phase system by acidifying the mixture with inorganic acids or strong organic acids, such as, for example, sulphuric acid, hydrochloric acid, formic acid or acetic acid, the organic solvent is distilled off in the open, in vacuo or with steam. Then the basic reaction product is set free and precipitated from the aqueous solution or suspension of its salt by adding alkali.

The process according to the invention makes it possible to manufacture compounds which have a high value, for example as intermediate products for organic syntheses, in high yields and very good purity in a manner which is particularly simple industrially. With regard to these characteristics, it is considerably superior to the most closely comparable known processes.

In the following illustrative embodiments of the invention, all the parts are parts by weight and all the percentages are percentages by weight.

EXAMPLE 1

191 parts of benzenesulphonyl chloride are added to a mixture of 109 parts of m-aminophenol, 500 parts of water, 880 parts of chlorobenzene, 21.2 parts of sodium carbonate and 4.6 parts of trialkyl-($C_8$-$C_{10}$)-methylammonium chloride in the course of 2 hours at 35°–40° C. and at pH 10.5–10.8, whilst stirring, the pH value being kept in the range indicated with about 170 parts of 27% strength sodium hydroxide solution. After the addition of the sulphochloride, the mixture is acidified with about 140 parts of 50% strength sulphuric acid, the chlorobenzene is distilled off with steam and the product is precipitated by neutralisation with sodium hydroxide solution. After drying, 257.3 parts of product of melting point 43°–45° C. are obtained with a 3'-amino-benzenesulphonic acid phenyl ester content of 90%. The yield is 93% of theory.

Instead of the 21.2 parts of sodium carbonate, 27.6 g of potassium carbonate can also be employed.

If only 2.3 parts of trialkyl-($C_8$-$C_{10}$)-methylammonium chloride are employed, a yield of 3'-aminp-benzenesulphonic acid phenyl ester of 90% of theory is obtained.

If 9.2 parts of trialkyl-($C_8$-$C_{10}$)-methylammonium chloride are employed instead of the 4.6 parts employed above, 3'-amino-benzenesulphonic acid phenyl ester is also obtained in a yield of 93% of theory.

EXAMPLE 2

191 parts of benzenesulphonyl chloride are added to a mixture of 109 parts of m-aminophenol, 500 parts of water, 880 parts of chlorobenzene, 21.2 parts of sodium carbonate and 5.3 parts of tetrabutylammonium chloride in the course of 2 hours at 35°–40° C. and pH 10.5–10.8, whilst stirring, the pH value being kept in the range indicated with about 170 parts of 27% strength sodium hydroxide solution. After the addition of the sulphochloride, the mixture is acidified with about 140 parts of 50% strength sulphuric acid, the chlorobenzene is distilled off with steam and the product is precipitated by neutralisation with sodium hydroxide solution. After drying, 258 parts of product of melting point 44°–47° C. are obtained with a 3'-amino-benzenesulphonic acid phenyl ester content of 87%.

Yield: 90% of theory.

If the reaction is carried out according to Example 2, but using 4.2 parts of didodecyl-dimethylammonium chloride instead of 5.3 parts of tetrabutylammonium chloride, a yield of 3'-amino-benzenesulphonic acid phenyl ester of 85% of theory is obtained.

EXAMPLE 3

191 parts of benzenesulphonyl chloride are added to a mixture of 109 parts of o-aminophenol, 500 parts of water, 880 parts of chlorobenzene, 21.2 parts of sodium carbonate and 4.6 parts of trialkyl-($C_8$-$C_{10}$)-methylammonium chloride in the course of 2 hours at 35°–40° C. and at pH 10.4–10.7, whilst stirring, the pH being kept in the range indicated with about 170 parts of 27% strength sodium hydroxide solution. If the further procedure followed is as indicated in Example 1, 262 parts of product are obtained with a 2'-amino-benzenesulphonic acid phenyl ester content of 83.6%.

Yield 88% of theory.

Melting point: 70°–75° C.

Similarly good yields of 2'-amino-benzenesulphonic acid phenyl ester are obtained when equivalent amounts of the following phase transfer catalysts are employed instead of the trialkyl-($C_8$-$C_{10}$)-methylammonium chloride used in Example 3: tetrabutylammonium chloride and benzyltrimethylammonium chloride.

If the reaction is carried out according to Example 3 but without adding trialkyl-($C_8$-$C_{10}$)-methylammonium chloride, a yield of 2'-amino-benzenesulphonic acid phenyl ester of 78% of theory is obtained.

EXAMPLE 4

191 parts of benzenesulphonyl chloride are added to a mixture of 109 parts of m-aminophenol, 500 parts of water, 880 parts of toluene, 21.2 parts of sodium carbonate and 4.6 parts of trialkyl-($C_8$-$C_{10}$)-methylammonium chloride in the course of 2 hours at 35°–40° C. and at pH 10.5–10.8, whilst stirring, the pH value being kept in the range indicated with about 170 parts of 27% strength sodium hydroxide solution. After the addition of the sulphochloride, the mixture is acidified with about 140 parts of 50% strength sulphuric acid, the toluene is distilled off with steam and the product is precipitated by neutralisation with sodium hydroxide solution. After drying, 250.0 parts of product melting point 44°–45° C. are obtained with a 3'-amino-benzenesulphonic acid phenyl ester content of 90%.

The yield is 90% of theory.

Similarly high yields of 3'-amino-benzenesulphonic acid phenyl ester are obtained if the 880 parts of toluene employed in Example 4 are replaced by the same amount of 1,2-dichloroethane, o-dichlorobenzene, n-octane or o-chlorotoluene.

EXAMPLE 5

A solution of 208 parts of p-toluenesulphonic acid chloride in 275 parts of chlorobenzene is added to a mixture of 109 parts of m-aminophenol, 500 parts of water, 21.2 parts of sodium carbonate, 715 parts of chlorobenzene and 3.7 parts of tetrabutylammonium chloride in the course of 2 hours at 35°–40° C. at pH 10.4–10.7, whilst stirring, the pH value being kept in the range indicated with about 170 parts of 27% strength sodium hydroxide solution. If the reaction is further carried out as indicated in Example 1, 278 parts of 3'-amino-4-methyl-benzenesulphonic acid phenyl ester are obtained with a purity of 88%.

Yield: 93% of theory.
Melting point: 70°-74° C.

If the reaction is carried out according to Example 5, but using 4.2 parts of didodecyl-dimethylammonium chloride instead of the 3.7 parts of tetrabutylammonium chloride, a yield of 3'-amino-4-methyl-benenesulphonic acid phenyl ester of 85% of theory is obtained.

Similarly good yields of 3'-amino-4-methyl-benzenesulphonic acid phenyl ester are obtained if equivalent amounts of the following phase transfer catalysts are employed instead of the tetrabutylammonium chloride used in Example 5: di-octyl-dimethylammonium bromide, tridecyl-methyl-ammonium chloride or benzyltrimethylammonium chloride.

If the reaction is carried out according to Example 5, but without the addition of tetrabutylammonium chloride, a yield of 3'-amino-4-benzenesulphonic acid phenyl ester of 68% of theory is obtained with a purity of 66%.

EXAMPLE 6

191 parts of benzenesulphonic chloride are added to a mixture of 109 parts of m-aminophenol, 500 parts of water, 880 parts of chloroform, 28.0 parts of calcium carbonate amd 4.6 parts of trialkyl-($C_8$-$C_{10}$)-methylammonium chloride in the course of 2 hours at 35°-40° C. and at pH 10.5-10.8, whilst stirring, the pH value being kept in the range indicated with about 170 parts of 27% strength sodium hydroxide solution. After the addition of the sulphochloride, the mixture is acidified with about 143 parts of 36% strength hydrochloric acid, the chloroform is distilled off with steam and the product is precipitated by neutralisation with sodium hydroxide solution. After drying, 258.6 parts of product of melting poing 44°-46° C. are obtained with a 3'-amino-benzenesulphonic acid phenyl ester content 91%. The yield is 94.5% of theory.

The same end product is obtained in 90% yield if Example 6 is carried out at the reflux temperature of the reaction mixture.

By lengthening the period over which the benzenesulphonyl chloride and sodium hydroxide solution are added to 4.5 hours, it is also possible to carry out the reaction at 20°-22° C. In this case, a yield of 92.5% of theory is obtained.

EXAMPLE 7

A solution of 226 parts of p-chlorobenzenesulphonyl chloride in 330 parts of chlorobenzene is added to a mixture of 109 parts of m-aminophenol, 500 parts of water, 21.2 parts of sodium carbonate, 660 parts of chlorobenzene and 4.6 parts of trialkyl-($C_8$-$C_{10}$)-methylammonium chloride in the course of 2 hours at 35°-40° C. and at pH 10.5-10.8, whilst stirring, the pH value being kept in the range indicated with about 150 parts of 27% strength sodium hydroxide solution. If the further procedure followed is as indicated in Example 1, 3'-amino-4-chlorobenzenesulphonic acid phenyl ester is obtained in 80% purity and a yield of 95% of theory, relative to pure substance.

Melting point: 70°-72° C.

If the reaction is carried out as indicated in Example 7, but without trialkyl-($C_8$-$C_{10}$)-methylammonium chloride, a yield of 3'-amino-4-chlorobenzenesulphonic acid phenyl ester of 72% of theory is obtained, with a purity of 68% and a melting point of 58°-60° C.

The aromatic aminohydroxy compounds (starting material II) and aromatic sulphochlorides (starting material III) indicated in the table which follows can be reacted in a manner analogous to that described in Examples 1 to 7 to give end products according to the invention:

Table

| Starting material II | Starting material III | Organic solvent | pH | Temperature °C. | End product | yield % of theory | Melting point |
|---|---|---|---|---|---|---|---|
| 3-aminophenol (OH, NH2) | naphthalene-SO2Cl | chlorobenzene | 10.5-10.8 | 35-40 | naphthyl-SO2-O-phenyl-NH2 | 72 | 102°-104° C. |
| 3-aminophenol (OH, NH2) | O2N-phenyl-SO2Cl | chlorobenzene | 10.5-10.8 | 35-40 | O2N-phenyl-SO2-O-phenyl-NH2 | 81 | 140°-144° C. |
| 2-amino-3-hydroxynaphthalene (HO, NH2) | phenyl-SO2Cl | chlorobenzene | 10.3-10.6 | 35-40 | phenyl-O2SO-naphthyl-NH2 | 50 | 110°-115° C. |
| 4-amino-1-hydroxynaphthalene (OH, NH2) | phenyl-SO2Cl | chlorobenzene | 10.4-10.7 | 35-40 | O-SO2-phenyl on naphthyl-NH2 | 78 | 116°-120° C. |

We claim:
1. A process for the manufacture of esters of aromatic sulphonic acids and aromatic aminohydroxy compounds of the formula I

$$H_2N-A-O-SO_2-B \qquad (I)$$

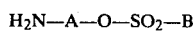

comprising reacting an aromatic aminohydroxy compound of the formula II $$H_2N—A—OH \quad (II)$$

having a $pK_a$ value of from 8.5 to 10.1, with a sulphochloride of the formula III $$Cl—SO_2—B \quad (III)$$

wherein
  A is phenylene, substituted phenylene, naphthylene are substituted naphthylene,
  B is phenyl, substituted phenyl, naphthyl or substituted naphthyl, and both A and B are from —COOH and —SO$_3$H substituents;
  the reaction taking place in a reaction medium consisting essentially of water and a water-immiscible organic solvent for the sulphochloride, at a temperature of from 0° to 95° C., at a pH which is determined from and associated with the $pK_a$ value of said aromatic aminohydroxy compound of formula II by the equation $$pK_a - pH = 0.5 \text{ to } -1.5,$$

and in the presence of a phase transfer catalyst which is a quaternary ammonium salt or a phosphonium salt.

2. A process according to claim 1 wherein A is phenylene or naphthylene.

3. A process according to claim 1, wherein A is substituted phenylene or substituted naphthylene having from one to three identical or different substituents each of which is selected from the group consisting of halogen, alkyl having 1 to 5 C atoms, cycloalkyl having 3 to 6 C atoms, alkenyl having 2 to 6 C atoms, phenyl, alkoxy having 1 to 6 C atoms, and alkanoyl having a total of 1 to 7 C atoms.

4. A process according to claim 1, wherein A is substituted phenylene or substituted naphthylene having one substituent selected from the group consisting of alkyl having 1 to 3 C atoms, fluorine, chlorine and bromine.

5. A process according to claim 1 wherein B is phenyl.

6. A process according to claim 1 wherein B is substituted phenyl having one or two identical or different substituents each of which is selected from the group consisting of halogen, nitro, cyano, alkyl having 1 to 6 C atoms and alkanoyl having a total of 1 to 6 C atoms.

7. A process according to claim 1 wherein B is substituted phenyl having one substituent which is selected from the group consisting of fluorine, chlorine, bromine and alkyl having 1 to 6 C atoms.

8. A process according to claim 1 wherein B is naphthyl.

9. A process according to claim 1 wherein B is substituted naphthyl having one substituent selected from the group consisting of halogen, nitro, cyano, and alkyl with 1 to 6 C atoms.

10. A process according to claim 1 wherein the phase transfer catalyst is a quaternary ammonium salt or phosphonium salt of the formula IV or V, respectively $$\left[\begin{array}{c} R_9 \\ | \\ R_8—N^{\oplus}—R_6 \\ | \\ R_7 \end{array}\right] X^{\ominus} \quad \left[\begin{array}{c} R_9 \\ | \\ R_8—P—R_6 \\ | \\ R_7 \end{array}\right] X^{\ominus}$$

(IV) (V)

wherein $R_6$, $R_7$, $R_8$ and $R_9$ are the same or different and each is selected from the group consisting of alkyl having 1 to 16 C atoms, hydroxy-alkyl having 2 to 16 C atoms, alkoxyalkyl having 1 to 16 C atoms, phenyl, alkylphenyl having 1 to 10 C atoms in the alkyl radical, benzyl and phenethyl; and wherein $X^{\ominus}$ is selected from the group consisting of $F^{\ominus}$, $Cl^{63}$, $Br^{\ominus}$, $SO_4^{\ominus\ominus}$, $HSO_4^{\ominus}$, $SO_3^{\ominus\ominus}$ or $HSO_3^{\ominus}$.

11. A process according to claim 10 wherein the phase transfer catalyst is selected from the group consisting of di-(dodecyl)-dimethylammonium chloride, hexadecyltrimethylammonium chloride, tetrabutylammonium chloride, trioctylmethylammonium chloride, tris-decylmethylammonium chloride and trialkyl-($C_8$-$C_{10}$ mixture)-methylammonium chloride.

12. A process according to claim 11 wherein from 0.2 to 2.5 mol% of the phase transfer catalyst relative to the amount of the compound of formula II is employed.

13. A process according to claim 1, wherein A is phenylene, naphthylene, chloro-phenylene, fluoro-phenylene, bromo-phenylene, dichloro-phenylene, dibromo-phenylene, chloro-bromo-phenylene, methylphenylene, ethyl-phenylene, hexyl-phenylene, cyclohexyl-phenylene, vinyl-phenylene, allyl-phenylene, dimethyl-phenylene, methyl-butyl-phenylene, methyl-hexyl-phenylene, ethyl-propyl-phenylene, methyl-vinyl-phenylene, methyl-allyl-phenylene, ethyl-chloro-phenylene, propyl-chloro-phenylene, methyl-fluoro-phenylene, methylchloro-vinyl-phenylene, methyl-bromophenylene, cyclohexyl-fluoro-phenylene, phenyl-phenylene, methoxy-phenylene, ethoxy-phenylene, acetyl-phenylene, butyryl-phenylene, benzoyl-phenylene, valeryl-phenylene.

14. A process according to claim 1, wherein B is phenyl, naphthyl, chloro-phenyl, fluoro-phenyl, bromo-phenyl, dichloro-phenyl, nitro-phenyl, cyano-phenyl, methyl-phenyl, ethyl-phenyl, hexyl-phenyl, acetyl-phenyl.

* * * * *